United States Patent
Duncan et al.

(10) Patent No.: US 10,203,357 B2
(45) Date of Patent: Feb. 12, 2019

(54) DYNAMIC BODY VOLTAGE TESTING

(71) Applicant: Seagate Technology LLC, Cupertino, CA (US)

(72) Inventors: Kevin Scott Duncan, Shakopee, MN (US); Dale Parkin, Rosemount, MN (US)

(73) Assignee: SEAGATE TECHNOLOGY LLC, Cupertino, CA (US)

(*) Notice: Subject to any disclaimer, the term of this patent is extended or adjusted under 35 U.S.C. 154(b) by 0 days.

(21) Appl. No.: 15/611,197

(22) Filed: Jun. 1, 2017

(65) Prior Publication Data
US 2018/0348263 A1    Dec. 6, 2018

(51) Int. Cl.
| | |
|---|---|
| *G01R 19/155* | (2006.01) |
| *A61B 5/05* | (2006.01) |
| *A61B 5/00* | (2006.01) |
| *E06B 11/08* | (2006.01) |
| *E06B 11/02* | (2006.01) |
| *G01R 29/12* | (2006.01) |

(52) U.S. Cl.
CPC ............ *G01R 19/155* (2013.01); *A61B 5/05* (2013.01); *A61B 5/6887* (2013.01); *A61B 5/742* (2013.01); *A61B 5/7405* (2013.01); *A61B 5/7475* (2013.01); *E06B 11/022* (2013.01); *E06B 11/08* (2013.01); *G01R 29/12* (2013.01)

(58) Field of Classification Search
CPC .................................................. G01R 29/12
See application file for complete search history.

(56) References Cited

U.S. PATENT DOCUMENTS

| | | | | |
|---|---|---|---|---|
| 4,649,374 | A | * 3/1987 | Hoigaard | G01R 27/20 128/908 |
| 4,857,916 | A | * 8/1989 | Bellin | G06K 9/00375 340/5.52 |
| 5,348,784 | A | 9/1994 | Lampert | |
| 5,422,630 | A | 6/1995 | Quinn et al. | |
| 5,666,106 | A | * 9/1997 | Nasman | G08B 21/182 324/510 |
| 6,671,160 | B2 | 12/2003 | Hayden | |
| 6,873,516 | B1 | 3/2005 | Epstein | |
| 6,930,612 | B1 | 8/2005 | Kraz et al. | |
| 7,353,120 | B2 | 4/2008 | Enta | |
| 7,817,057 | B2 | 10/2010 | Bumanlag et al. | |

(Continued)

OTHER PUBLICATIONS

"ESD Body Walking Voltage Measurement Demonstration", Dangelmayer Associates, published on Oct. 22, 2012, https://www.youtube.com/watch?v=DXF7SldzQVM&t=337s, 14 pages.

*Primary Examiner* — Clayton E Laballe
*Assistant Examiner* — Jas Sanghera
(74) *Attorney, Agent, or Firm* — Westman, Champlin & Koehler, P.A.

(57) ABSTRACT

A system includes an electrically conductive handle, a detector, and a controller. The electrically conductive handle is configured to move along a fixed handle path relative to a floor. The detector is electrically coupled to the handle and is configured to detect at least one of a voltage or an electrical charge at the handle during movement of the handle relative to the floor along the handle path. The controller is configured to initiate an event based upon the voltage or charge detected at the handle during movement of the handle relative to the floor along the handle path.

18 Claims, 4 Drawing Sheets

(56) References Cited

U.S. PATENT DOCUMENTS

| | | |
|---|---|---|
| 8,963,552 B2 | 2/2015 | Savich |
| 9,363,934 B2 | 6/2016 | Campbell et al. |
| 2004/0046401 A1* | 3/2004 | Watanabe ............... E05F 15/63 292/262 |
| 2008/0256998 A1 | 10/2008 | Mallian et al. |

* cited by examiner

DYNAMIC BODY VOLTAGE TESTING

BACKGROUND

The problem of electrostatic discharge (ESD) is well known, particularly for those who handle sensitive electronic equipment. Static electricity charges can build up on a person when they move. When such an electrostatically-charged person touches an electrically conductive object, an electrical current may be discharged from the person to the object due to the voltage potential difference between the person and object. If the electrically conductive object is sensitive electronic equipment, that equipment may be damaged by the discharged electrical current.

SUMMARY

Embodiments of the present disclosure are generally directed to systems and methods for evaluating human subjects for electrostatic discharge (ESD) threats. These evaluations can include evaluations of the subject in combination with ESD flooring, ESD footwear, and/or combinations of ESD flooring and footwear.

One embodiment of the system includes an electrically conductive handle, a detector, and a controller. The electrically conductive handle is configured to move along a fixed handle path relative to a floor. The detector is electrically coupled to the handle and is configured to detect at least one of a voltage or an electrical charge at the handle during movement of the handle relative to the floor along the handle path. The controller is configured to initiate an event based upon the voltage or charge detected at the handle during movement of the handle relative to the floor along the handle path.

In one embodiment of the method, a subject is electrically connected to a voltage or charge detector through an electrically conductive handle. The handle is configured to move along a fixed handle path relative to a floor. The handle is moved along the handle path while the subject walks over the floor. A voltage or an electrical charge at the handle is detected during movement of the handle using a detector that is electrically coupled to the handle. An event is initiated based upon the detected voltage or charge during movement of the handle relative to the floor along the handle path using a controller comprising a microprocessor.

This Summary is not intended to describe each disclosed embodiment or every implementation of dynamic body voltage testing. Many other novel advantages, features, and relationships will become apparent as this description proceeds. The figures and the description that follow more particularly exemplify illustrative embodiments.

DETAILED DESCRIPTION OF ILLUSTRATIVE EMBODIMENTS

Figure 1:
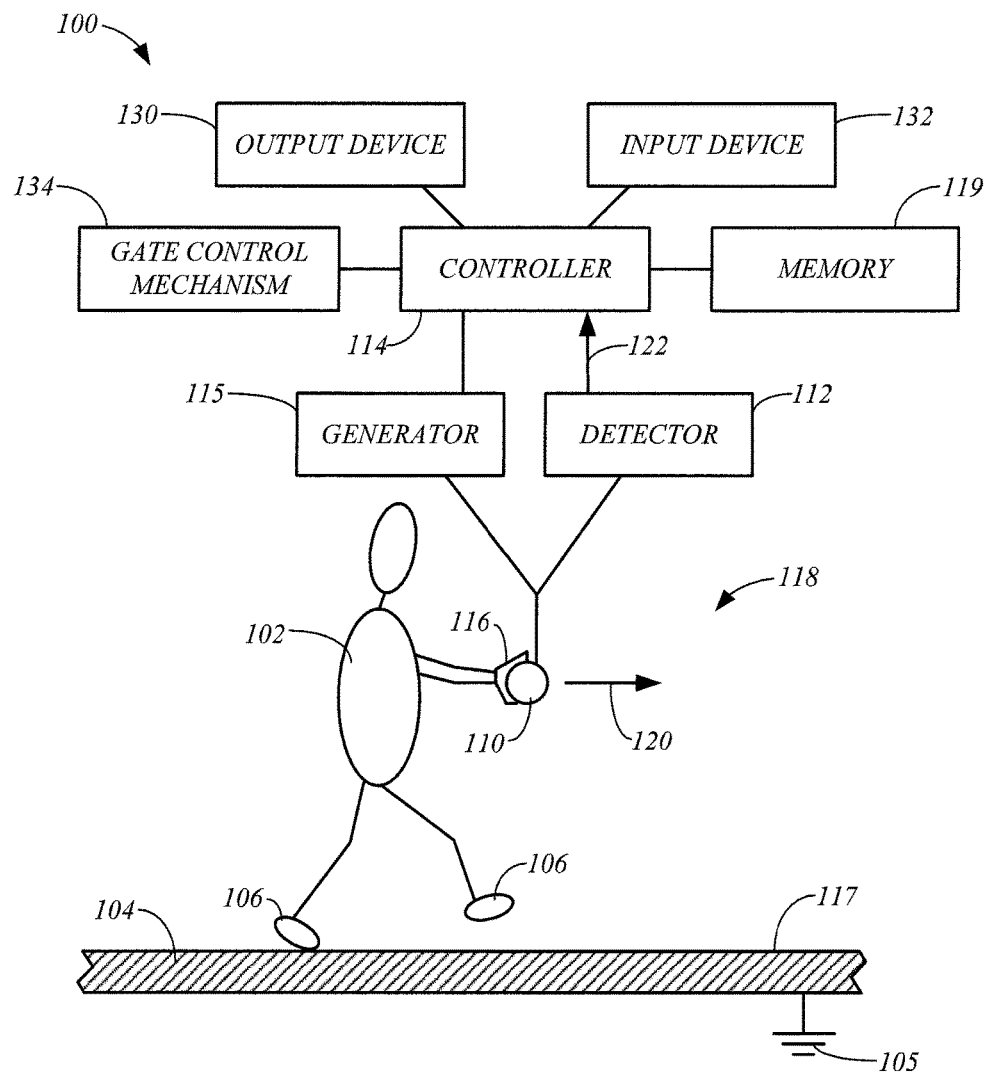
FIG. 1 is a simplified diagram of a dynamic body voltage testing system and a subject under test, in accordance with embodiments of the present disclosure.

Embodiments of the present disclosure are described more fully hereinafter with reference to the accompanying drawings. Elements that are identified using the same or similar reference characters refer to the same or similar elements. The various embodiments of the present disclosure may, however, be embodied in many different forms and should not be construed as limited to the embodiments set forth herein. Rather, these embodiments are provided so that this disclosure will be thorough and complete, and will fully convey the scope of the present disclosure to those skilled in the art.

Specific details are given in the following description to provide a thorough understanding of the embodiments. However, it is understood by those of ordinary skill in the art that the embodiments may be practiced without these specific details. For example, circuits, systems, networks, processes, frames, supports, connectors, motors, processors, and other components may not be shown, or shown in block diagram form in order to not obscure the embodiments in unnecessary detail.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element is referred to as being "connected," "coupled," or "attached" to another element, it can be directly connected, coupled or attached to the other element, or it can be indirectly connected, coupled, or attached to the other element where intervening or intermediate elements may be present. In contrast, if an element is referred to as being "directly connected," "directly coupled" or "directly attached" to another element, there are no intervening elements present. Drawings illustrating direct connections, couplings or attachments between elements also include embodiments, in which the elements are indirectly connected, coupled or attached to each other.

It will be understood that, although the terms first, second, etc. may be used herein to describe various elements, these elements should not be limited by these terms. These terms are only used to distinguish one element from another. Thus, a first element could be termed a second element without departing from the teachings of the present disclosure.

Unless otherwise defined, all terms (including technical and scientific terms) used herein have the same meaning as commonly understood by one of ordinary skill in the art relating to the present disclosure. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As will further be appreciated by one of skill in the art, embodiments of the present disclosure may be embodied as methods, systems, devices, and/or computer program products, for example. Accordingly, embodiments of the present disclosure may take the form of an entirely hardware embodiment, an entirely software embodiment or an embodiment combining software and hardware aspects. The computer program or software aspect of embodiments of the present disclosure may comprise computer readable instructions or code stored in a computer readable medium or memory. Execution of the program instructions by one or more processors (e.g., central processing unit) results in the one or more processors performing one or more functions or method steps described herein. Any suitable patent subject matter eligible computer readable media or memory may be utilized including, for example, hard disks, CD-ROMs, optical storage devices, or magnetic storage devices. Such computer readable media or memory do not include transitory waves or signals.

Computer program or software aspects of embodiments of the present disclosure may comprise computer readable instructions or code stored in a computer readable medium or memory. Execution of the program instructions by one or more processors (e.g., central processing unit or controller) results in the one or more processors performing one or more functions or method steps described herein. Any suitable patent subject matter eligible computer readable media or memory may be utilized including, for example, hard disks, CD-ROMs, optical storage devices, or magnetic storage devices. Such computer readable media or memory do not include transitory waves or signals.

Embodiments of the present disclosure may also be described using flowchart illustrations and block diagrams. Although a flowchart or block diagram may describe the operations as a sequential process, many of the operations can be performed in parallel or concurrently. In addition, the order of the operations may be re-arranged. In addition, the order of the operations may be re-arranged. Embodiments of methods described herein include not preforming method steps and embodiments described herein. A process is terminated when its operations are completed, but could have additional steps not included in a figure or described herein.

Electrostatic discharge (ESD) control programs generally utilize special flooring and footwear to control ESD when mobility is desired. ESD flooring, such as an electrically grounded mat, is generally used to draw static electricity off personnel. ESD footwear is generally used to dissipate electrical charge to the ground, such as to ESD flooring. The ESD footwear may also maintain a high level of electrical resistance to limit a rate at which an electrical charge may travel through the footwear.

ESD flooring/footwear systems typically undergo product qualification and compliance verification testing to determine if threshold ESD requirements are met for an electrostatic protected area. The product qualification test evaluates ESD flooring and footwear components separately under controlled environmental conditions. The ESD flooring and footwear components are then tested again under the same environmental conditions in combined flooring/footwear systems. When a flooring/footwear system meets the ESD threshold requirements, it may be "approved" for use inside the electrostatic protected area. Any changes to the approved flooring/footwear system would require the product qualification test to be repeated.

The compliance verification test involves testing the footwear and/or flooring system in combination with a person in a static (stationary) position. This testing measures the system's electrical resistance, such as the electrical resistance along a path from the person through the footwear to a metal plate or grounded flooring system. The system's resistance is then used as a correlation to the previous product qualification values to ensure that the footwear is still functioning as intended.

Embodiments of the present disclosure are generally directed to systems and methods for evaluating subjects for electrostatic discharge (ESD) threats. These evaluations can include evaluations of the subject in combination with ESD flooring, ESD footwear, and/or combinations of ESD flooring and footwear. Additionally, these evaluations may occur while the subject moves (dynamic body voltage test) and/or while the subject is substantially stationary (system resistance test). As a result, embodiments of the systems and methods of the present disclosure may be used to simultaneously perform in-situ product qualification and compliance verification testing, while providing actual human body model voltage threats instead of traditional correlated values. Embodiments of the present disclosure also provide additional advantages over conventional ESD flooring/footwear testing.

FIG. 1 is a simplified diagram of a dynamic body voltage testing system 100 and a human subject 102 under test, in accordance with embodiments of the present disclosure. In some embodiments, the evaluations performed by the system 100 include evaluations of ESD flooring 104, which is electrically grounded at 105, and/or ESD footwear 106. These evaluations are performed to determine whether the ESD flooring 104 and/or the ESD footwear 106 provides sufficient ESD protection to allow the subject 102 to enter an electrostatic protective area where, for example, the subject 102 may be required to contact sensitive electronic equipment.

Some embodiments of the system 100 include a handle 110, a voltage or charge detector 112, and a controller 114. In some embodiments, the system 100 includes a generator 115, which is generally used during static (electrical resistance) testing of the subject in combination with the ESD flooring 104 and/or the ESD footwear 106.

The handle 110 can be any suitable electrically conductive component that is configured for contact with the subject 102, such as the hands 116 of the subject 102, as shown in FIG. 1. Thus, the handle can take on any suitable form, such as a cylindrical bar, handle grips, or other component configured to be grabbed by the hands 116 of the subject 102. The handle 110 may also represent a component that provides an electrically conductive path from the subject 102 to another component of the system 100, such as the detector 112. Accordingly, in some embodiments, the handle 110 represents electrode leads, wrist straps, or other suitable component that facilitates an electrical connection between the subject 102 and the system 100.

In some embodiments, the handle 110 is configured to move along a fixed handle path relative to the floor 117, which may include ESD flooring 104. This generally limits the movement of the subject 102 to a test area 118 where components of the system 100 are located, and where ESD flooring 104 or other environmental conditions may be controlled.

The fixed handle path along which the handle 110 travels may be substantially fixed, such as when the handle 110 is rigid and closely follows (e.g., within 1 to 6 inches) a certain path. Alternatively, the fixed handle path along which the handle 110 travels may allow for more substantial movement of the handle 110 as it follows the fixed handle path. For example, the handle 110 may take the form of a bar or an electrode that is coupled to other components of the system 100 through a flexible component, such as a wire, which allows the handle 110 to move around while the subject 102 drives movement of the handle 110 along the fixed handle path. As a result, the fixed handle path for the handle 110 may still allow for substantial movement (e.g., 1-5 feet) while traveling along the predetermined fixed handle path within the test area 118.

Embodiments of the voltage or charge detector 112 are configured to detect a voltage or electrical charge on the handle 110. The voltage or charge detector 112 can take on any suitable form, and may utilize and implement conventional components and techniques. The detector includes an output 122, which indicates the detected charge or voltage.

In some embodiments, the controller 114 represents one or more processors that control components of the system 100 to perform one or more functions described herein, such as in response to the execution of instructions, which may be stored locally in memory 119 of the system 100, or in memory that is remote from the system 100. In some embodiments, the one or more processors of the controller 114 are components of one or more computer-based systems. In some embodiments, the controller 114 includes one or more control circuits, microprocessor-based engine control systems, one or more programmable hardware components, such as a field programmable gate array (FPGA), that are used to control components of the system 100 to perform one or more functions described herein.

In some embodiments, the controller 114 operates to perform a moving or dynamic body voltage (or charge) test on the subject 102. During this test, an electrical connection is established between the subject 102 and the detector 112 through the handle 110. This allows the detector 112 to monitor the electrical voltage or charge of the subject 102, such as relative to a common electrical ground 105, for example. The test subject 102 then walks within the test area 118 over the floor 117, which may or may not include ESD flooring 104, such as in the direction indicated by arrow 120. During this movement of the subject 102 and the handle 110, the controller 114 monitors the output 122 from the detector 112 to determine a voltage or electrical charge buildup on the subject 102. In some embodiments, the measured peak values of the voltage or electrical charge that accumulates on the subject 102 during movement across the floor 117 are compared to a threshold value to evaluate ESD flooring 104 within the test area 118, and/or ESD footwear worn by the subject 102, and to determine whether the subject 102 may enter the electrostatic protected area.

In some embodiments, the generator 115 is electrically coupled to the handle 110 and is configured to apply a preset charge or a preset voltage to the handle 110, which is generally used by the system to perform a static test of the electrical resistance of the subject 102 in combination with ESD flooring 104 and/or ESD footwear 106. The generator 115 can take on any suitable form to apply the preset voltage or charge to the handle 110 in accordance with known techniques.

In some embodiments, the controller 114 is used to evaluate a decay time at which a preset charge or voltage may be dissipated through the subject 102 within the test area 118 while the subject remains stationary. This allows the system 100 to evaluate the electrical resistance of ESD flooring 104 located in the test area 118, and/or ESD footwear 106 worn by the subject 102. In some embodiments, the controller 114 controls the generator 115 to apply a preset charge or voltage to the handle 110. During the application of the voltage or electrical charge to the handle 110 by the generator 115, the controller 114 may monitor the output 122 from the detector, which indicates an amplitude of the voltage or electrical charge of the handle 110, until the output 122 indicates that the voltage or electrical charge has reached the desired preset value. The subject 102 is then placed in contact with the handle 110 either directly, such as by grabbing the handle 110 with the subject's hands 116, or indirectly, such as through an electrical lead coupled to the handle 110, for example. The controller 114 then measures the decay time over which at least a portion of the preset charge or voltage is dissipated through the subject 102. The decay time relates to the electrical resistance of the subject 102 in combination with the ESD flooring 104 and/or the ESD footwear 106. A long decay time indicates a high electrical resistance, and a short decay time indicates a low electrical resistance. In some embodiments, the controller 114 compares the measured decay time to a threshold value to determine whether the subject 102 in combination with the ESD flooring 104 and/or the ESD footwear 106 meets the requirements of the electrostatic protected area.

In some embodiments, the system 100 includes an output device 130 that may be controlled by the controller 114 to produce a desired output. In some embodiments, the audible and/or visible signal produced by the output device 130 is configured to notify the subject 102 whether or not the subject 102 may enter an electrostatic protected area, and/or whether the subject 102 has passed or failed one or more tests performed by the system 100, for example. The output device 130 may also be used to lead the subject 102 through one or more testing procedures by providing instructions to the subject 102, such as, for example, when to hold the handle 110, when to hold still, when to walk, and/or other instructions.

In some embodiments, the output device 130 is configured to produce an audible signal and/or a visible signal. Thus, embodiments of the output device 130 may include a speaker, a display (e.g., a monitor), one or more lights, a buzzer, a mobile computing device (e.g., smartphone, laptop, etc.) and/or other suitable output devices configured to produce an audible and/or a visible signal.

In some embodiments, the system 100 includes an input device 132. The controller 114 may receive signals and/or information from the input device 132 that may be used during the testing procedure. The input device 132 may take on any suitable form. In some embodiments, the input device includes a barcode scanner, an ID card scanner, a keyboard, a microphone, a mouse, and/or another suitable input device. Using the input device 132, the controller 114 may, for example, acquire information regarding the subject 102, such as, for example, the name of the subject, the employee number associated with the subject, or other information. The controller 114 may also acquire settings and other testing information through the input device 132, such as, for example, information regarding the ESD flooring 104, information regarding the ESD footwear 106, testing parameters, and/or other information relating to the testing procedure.

In some embodiments, the system 100 includes a gate control mechanism 134, which assists in controlling access to an electrostatic protected area. For example, the gate control mechanism 134 may include a lock or latch on a gate or door, which may be deactivated by the controller 114 to allow the subject 102 to enter the electrostatic protected area in the event the testing determines that the subject 102 has qualified to enter the area. Other forms of gate control mechanisms 134 may also be used.

Figure 2:
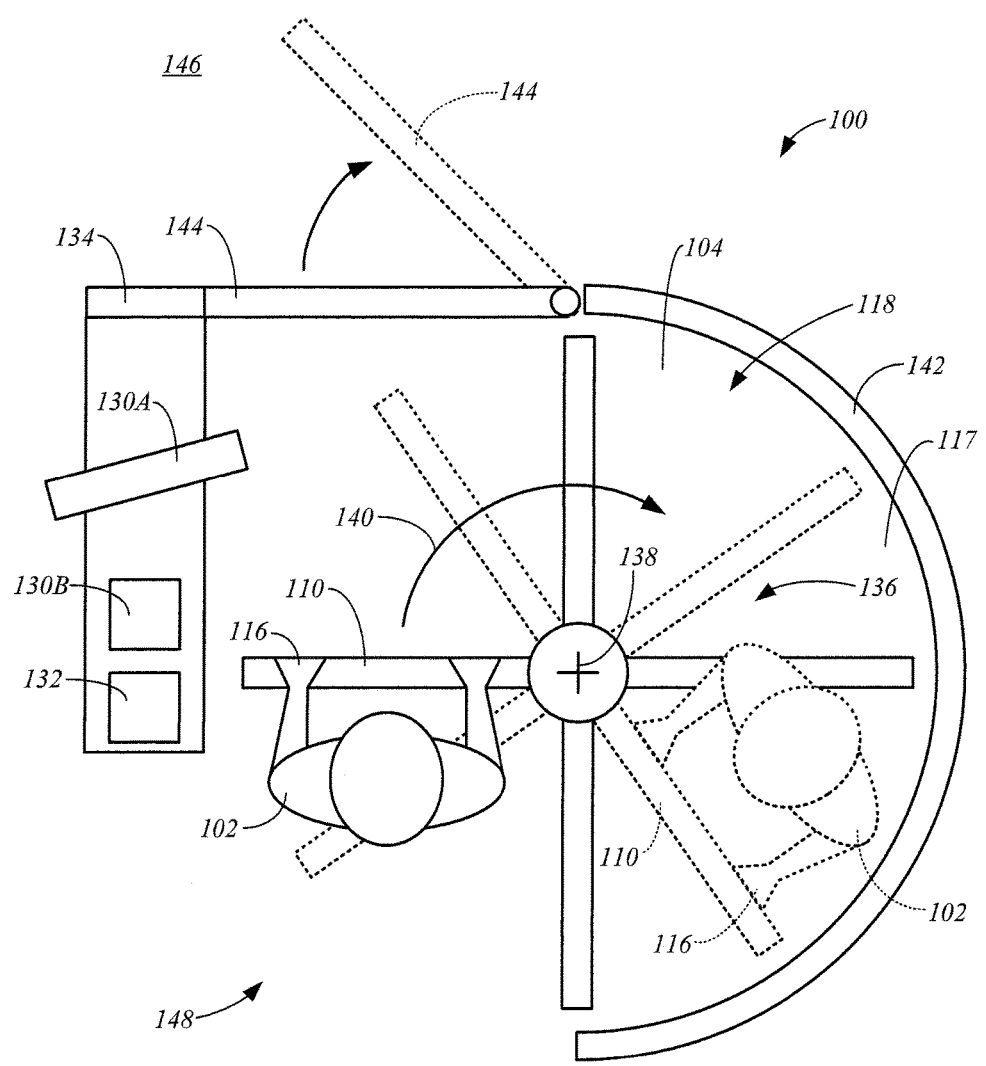
FIG. 2 is a simplified top view of a dynamic body voltage testing system and a subject under test, in accordance with embodiments of the present disclosure.
Figure 3:
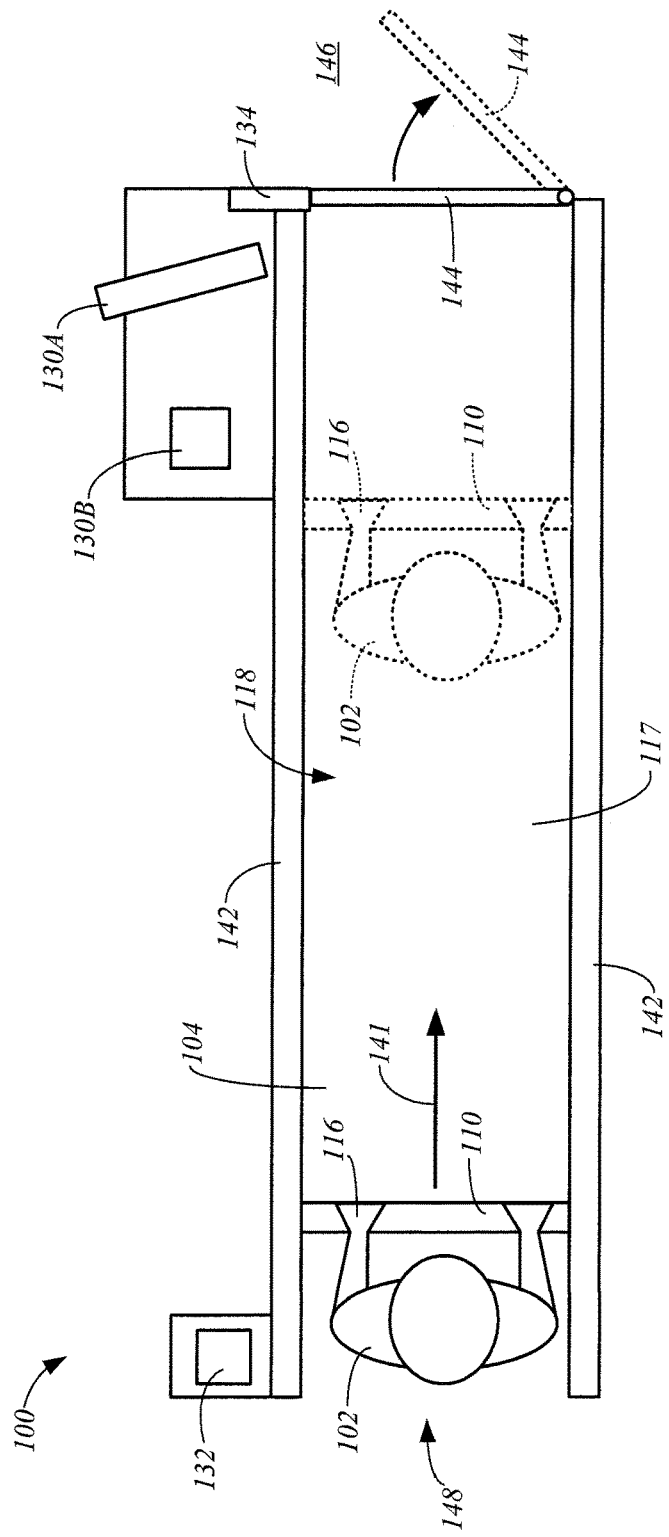
FIG. 3 is a simplified top view of an exemplary dynamic body voltage testing system and a subject under test in accordance with embodiments of the present disclosure.

FIGS. 2 and 3 are simplified top views of exemplary systems 100 with subjects 102 under test, in accordance with embodiments of the present disclosure. The exemplary system 100 illustrated in FIG. 2 includes a turnstyle 136 that includes one or more handles 110. The one or more handles 110 are configured to rotate about an axis 138. As a result, each of the handles 110 has a fixed circular path due to the rotation of the handles 110 about the axis 138, as indicated by arrow 140. In some embodiments, the one or more handles 110 of the system 100 are configured to move along a substantially linear path, such as indicated by arrow 141 in the exemplary system 100 shown in FIG. 3.

Exemplary systems 100 shown in FIGS. 2 and 3 may include an input device 132 in the form of a card reader or other suitable input device. The systems 100 may also include output devices 130 in the form of a display (130A) and/or a speaker (130B), or other suitable output device 130.

In some embodiments, the system 100 includes at least one peripheral boundary 142 that at least partially encloses the testing area 118, as shown in FIGS. 2 and 3. The peripheral boundary 142 may take on any suitable form. In some embodiments, the peripheral boundary 142 includes a wall, a rail, or another suitable peripheral boundary. In some embodiments, the handle 110 may extend from the peripheral boundary 142 and into the testing area 118, as shown in FIG. 3.

In some embodiments, the peripheral boundary 142 includes a gate 144 having a closed position (solid lines), and an open position (phantom lines), as shown in FIGS. 2 and 3. The opening and closing of the gate 144 is controlled by the gate control mechanism 134. In some embodiments, the gate 144 controls access to an electrostatic protected area 146 located on the opposite side of the gate 144 from the testing area 118.

In some embodiments, the peripheral boundary 142 includes an opening 148, through which a subject 102 may enter the testing area 118. In some embodiments, the peripheral boundary 142 may include a gate (not shown) to close off the opening 148 and completely enclose the testing area 118.

Figure 4:
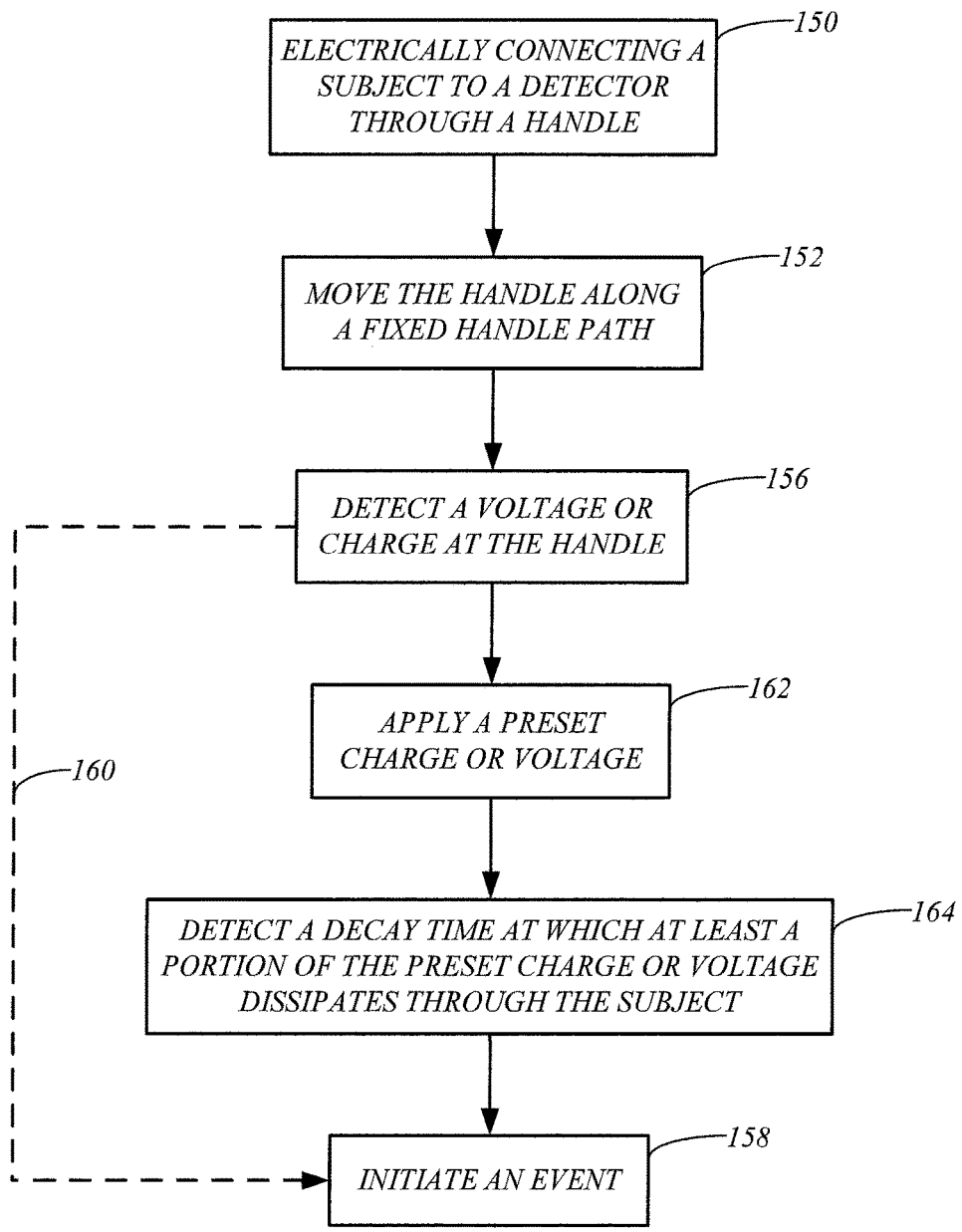
FIG. 4 is a flowchart illustrating a method in accordance with embodiments of the present disclosure.

FIG. 4 is a flowchart illustrating a method of using the system 100 to perform dynamic body voltage testing and/or static electrical resistance testing on a subject 102. At 150 of the method, a subject 102 is connected to a voltage or charge detector 112 through a handle 110. This may involve the subject 102 grabbing the handle 110 with subject's hands 116, as shown in FIGS. 1-3. Alternatively, the subject 102 may be connected to the detector 112 or the handle 110 through electrical leads, or another suitable device.

In some embodiments of the method, a dynamic body voltage test is performed on the subject. At 152 of the method, the subject 102 moves the handle 110 along a fixed handle path, as indicated by arrow 120 in FIG. 1. This generally involves the subject 102 walking on the floor 117 while remaining electrically connected to the detector 112 through the handle 110. In some embodiments, the subject 102 walks in a circular path 140 that corresponds to the circular fixed handle path 140, as indicated by the handle 110 and the subject 102 illustrated in phantom lines in FIG. 2. Alternatively, step 152 may involve the subject moving in a more linear path, such as path 150, as indicated by the handle 110 and the subject 102 illustrated in phantom lines in FIG. 3. Other fixed paths for the handle 110 may also be used.

At 156 of the method, a voltage or charge at the handle 110 is detected using the detector 112. For example, as mentioned above, the detector 112 may output a signal 120 indicating the amplitude of the voltage or electrical charge detected or sensed by the detector 112. In some embodiments of the method, the controller 114 initiates an event at 158 in response to the detected voltage or charge at the handle 110 in step 156, as indicated by line 160 in FIG. 4. Embodiments of the event initiated by the controller 114 in step 158 will be discussed in greater detail below.

In some embodiments of the method, either before, following, or in the place of steps 152 and 156 of the method, a static electrical resistance test is performed on the subject. At step 162 of the method, a preset electrical charge or voltage is applied to the handle 110 by the generator 115. At 164 of the method, the controller 114 uses the detector 112 to detect or measure a decay time, at which at least a portion of the preset electrical charge or voltage dissipates through the subject 102 and to electrical ground 105. In some embodiments of the method, the controller 114 initiates an event at 158 in response to the detected decay time.

Based on the voltage or electrical charge detected at the handle 110 in step 156, and/or the decay time detected in step 164, the controller 114 may initiate an event at step 158. In some embodiments, the event indicates whether the subject 102 is qualified to enter the electrostatic protected area 146 by meeting electrostatic discharge requirements, such as a voltage threshold value during the dynamic body voltage test, and/or a decay time or resistance threshold value during the static resistance test. The threshold values may be acquired by the controller 114 from the memory 119, from the input device 132, or from another location. The controller compares the measured voltage or voltages acquired in step 156 during the dynamic body voltage test and/or the decay time or resistance determined during step 164 of the static electrical resistance test to their corresponding voltage and decay time threshold values, and initiates the event in step 158.

For instance, if the measured voltage or voltages (step 156) meets a predetermined relationship to the voltage threshold value (e.g., measured voltage is less than the voltage threshold value), then the controller 114 can initiate an event that indicates that the subject 102 may enter the electrostatic protected area 146. If the measured voltage or voltages (step 156) do not meet the predetermined relationship to the voltage threshold value, then the controller 114 can initiate an event that indicates that the subject 102 may not enter the electrostatic protected area 146. Similarly, if the measured or detected decay time (step 164) meets a predetermined relationship to the decay time threshold value (e.g., the decay time is greater than the decay time threshold value), then the controller 114 initiates an event that indicates that the subject 102 may enter the electrostatic protected area 146. Similarly, if the measured or detected decay time (step 164) does not meet the predetermined relationship to the decay time threshold value, then the controller 114 initiates an event that indicates that the subject 102 may not enter the electrostatic protected area 146. In some embodiments, the controller initiates an event (step 158) that indicates that the subject 102 may enter the electrostatic protected area only when the measured voltage and the measured decay time meet the predetermined relationships to their corresponding threshold values.

In some embodiments, the event may include the production of one or more audible and/or visible signals using one or more output devices 130, such as using the display device 130A and/or the speaker 130B, for example. Additionally, the event may also include unlocking or opening the gate 144 using the gate control mechanism 134 to allow the subject 102 to enter the electrostatic protected area 146 when the electrostatic discharge requirements have been met. Likewise, when the electrostatic discharge requirements have not been met, the event may involve maintaining the gate 144 in the closed and/or locked position to prevent the subject 102 from entering the electrostatic protected area.

The above-disclosed subject matter is to be considered illustrative, and not restrictive, and the appended claims are intended to cover all such modifications, enhancements, and other embodiments, which fall within the scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A system comprising:
   an electrically conductive handle configured to move along a fixed handle path relative to a floor that comprises electrically grounded flooring;
   a detector electrically coupled to the handle and configured to detect a voltage or a charge at the handle during movement of the handle relative to the floor along the handle path; and
   a controller including a microprocessor, the controller configured to initiate an event based upon the voltage or charge detected at the handle during movement of the handle relative to the floor along the handle path.

2. The system according to claim 1, wherein:
   the system comprises a generator electrically coupled to the handle and configured to apply a preset charge or a preset voltage to the handle;
   the detector is configured to detect a decay time, at which at least a portion of the preset charge or voltage drains from the handle through a subject holding the handle; and
   the controller is configured to initiate the event based upon the decay time.

3. The system according to claim 1, further comprising an output device, wherein the event includes producing at least one of an audible signal and a visible signal using the output device.

4. The system according to claim 1, further comprising:
   a gate; and
   a gate control mechanism configured to control opening or unlocking the gate;
   wherein the event includes opening or unlocking the gate using the gate control mechanism.

5. The system according to claim 1, wherein the floor comprises electrostatic flooring that is electrically grounded.

6. The system according to claim 1, wherein the handle is configured to rotate about an axis.

7. The system according to claim 6, further comprising a turnstyle gate including the handle.

8. The system according to claim 1, further comprising a peripheral boundary to a walking path on the floor that corresponds to the handle path.

9. The system according to claim 8, wherein the handle extends from the peripheral boundary.

10. The system according to claim 1, further comprising an input device configured to receive subject identification information.

11. A method comprising:
    electrically connecting a subject including electrostatic footwear to a voltage or charge detector through an electrically conductive handle that is configured to move along a fixed handle path relative to a floor that comprises electrostatic discharge flooring coupled to electrical ground;
    moving the handle along the handle path while the subject walks over the floor;
    detecting a voltage or a charge at the handle during moving the handle using the detector; and
    initiating an event based upon the detected voltage or charge during the movement of the handle relative to the floor along the handle path using a controller comprising a microprocessor.

12. The method according to claim 11, wherein initiating an event comprises at least one of producing at least one of an audible signal and a visible signal using an output device, and opening or unlocking a gate using a gate control mechanism.

13. The method according to claim 11, further comprising:
    applying a preset charge or a preset voltage to the handle using a generator that is electrically coupled to the handle;
    detecting a decay time at which at which at least a portion of the preset charge or voltage dissipates through the subject using the detector; and
    initiating the event comprises initiating an event based upon the decay time using the controller.

14. The method according to claim 11, wherein walking the handle comprises rotating the handle about an axis.

15. A system comprising:
    a turnstyle gate comprising an electrically conductive handle configured to move along a circular handle path relative to a floor;
    a detector electrically coupled to the handle and configured to detect a voltage or a charge at the handle during movement of the handle relative to the floor along the handle path;
    an output device; and
    a controller including a microprocessor, the controller configured to produce at least one of an audible signal and a visible signal using the output device based upon the voltage or charge detected at the handle during movement of the handle relative to the floor along the handle path.

16. The system according to claim 15, further comprising:
    a gate; and
    a gate control mechanism configured to control opening or unlocking the gate;
    wherein the controller is configured to open or unlock the gate using the gate control mechanism based upon at least one of the voltage or charge detected at the handle during movement of the handle relative to the floor along the handle path.

17. The system according to claim 16, wherein:
    the system comprises a generator electrically coupled to the handle and configured to apply a preset charge or a preset voltage to the handle;
    the detector is configured to detect a decay time, at which at least a portion of the preset charge or voltage drains from the handle through a subject holding the handle; and
    the controller is configured to produce at least one of the audible signal and the visible signal using the output device based upon the decay time.

18. The system according to claim 16, further comprising a peripheral boundary to a walking path on the floor that corresponds to the circular handle path, the peripheral boundary extending from the gate.

* * * * *